United States Patent [19]

Strasser et al.

[11] Patent Number: 4,838,282

[45] Date of Patent: Jun. 13, 1989

[54] BONE BIOPSY NEEDLE ASSEMBLY

[75] Inventors: Robert K. Strasser, Nashua, N.H.; Robert L. Netsch, Spirit Lake, Iowa

[73] Assignee: Manan Manufacturing Co., Inc., Skokie, Ill.

[21] Appl. No.: 19,062

[22] Filed: Feb. 26, 1987

[51] Int. Cl.⁴ ............................................. A61B 10/00
[52] U.S. Cl. ..................................... 128/754; 128/310
[58] Field of Search ................ 128/749, 751, 753–754, 128/305, 310; 604/263

[56] References Cited

U.S. PATENT DOCUMENTS

| | | | |
|---|---|---|---|
| 3,850,158 | 11/1974 | Elias et al. | 128/754 |
| 3,913,566 | 10/1975 | Lacey | 128/754 |
| 4,022,191 | 5/1977 | Jamshidi | 128/753 |
| 4,141,365 | 2/1979 | Fischell et al. | |
| 4,256,119 | 3/1981 | Gauthier | 128/754 |
| 4,262,676 | 4/1981 | Jamshidi | 128/753 |
| 4,314,565 | 2/1982 | Lee | 128/754 X |
| 4,326,519 | 4/1982 | D'Alo et al. | |
| 4,356,828 | 11/1982 | Jamshidi | 128/754 |
| 4,403,617 | 9/1983 | Tretinyak | 128/754 |
| 4,430,080 | 2/1984 | Pasquini et al. | 604/263 X |
| 4,469,109 | 9/1984 | Mehl | 128/754 X |
| 4,487,209 | 12/1984 | Mehl | 128/754 |
| 4,513,754 | 4/1985 | Lee | 128/753 |
| 4,630,616 | 12/1986 | Tretinyak | 128/753 |
| 4,636,201 | 1/1987 | Ambrose et al. | 604/263 X |
| 4,655,226 | 4/1987 | Lee | 128/754 |

Primary Examiner—Kyle L. Howell
Assistant Examiner—Angela D. Sykes
Attorney, Agent, or Firm—Faegre & Benson

[57] ABSTRACT

A bone biopsy needle assembly is disclosed for withdrawing samples of bone, bone marrow and bone marrow cavity fluids as may be required in biopsy and transplant procedures. The assembly comprises a cannula having a sharpened distal end and a stylet, also having a sharpened distal end, coaxially received in the cannula lumen. The handles of the cannula and the stylet are provided with particular features for mating reception when assembled together to assure their secure alignment during the various operations required in use.

10 Claims, 2 Drawing Sheets

BONE BIOPSY NEEDLE ASSEMBLY

BACKGROUND OF THE INVENTION

1. Description of the Prior Art

It is often necessary to obtain samples of bone and to penetrate to the bone marrow cavity, to withdraw bone marrow or other bone marrow cavity fluids for such purposes as diagnostic study or for obtaining sufficient quantity of bone marrow to be used in transplant procedures.

In penetrating the hard, outer layer of marrow containing bones a sharpened surgical instrument such as a stylet, often fittingly mated within a cannula, is generally used. The instrument must be designed to allow the physician to exercise both the necessary pressure to penetrate the hard outer layer of the bone as well as extreme care to avoid unnecessary damage to bone and surrounding tissue. During the penetration procedure, the instrument must be able to be properly handled to avoid slipping in the outer surface of the bone and to allow proper positioning and orientation of the instrument, particularly when the bone marrow cavity must be reached.

Previous biopsy needles have presented disadvantages when used in this procedure. Often the handle does not allow maintaining a secure grip on the instrument, while also controlling the orientation of the stylet and cannula during the twisting and penetrating forces exercised in the bone penetration procedure. Representative of previously available biopsy needles are those described in U.S. Pat. Nos. 4,141,365, 4,256,119, 4,262,676, 4,326,519 4,487,209 and 4,513,754.

In the commonly assigned U.S. Pat. Nos. 4,403,617 and 4,630,616 there is disclosed a bone biopsy needle having a cannula and a stylet which is slideably received within the lumen of the cannula. The stylet has a handle rigidly attached to its proximal end, the handle having a broad, palm-contacting surface extending at right angles on either side of the axis of the stylet. The cannula has a handle-receiving recess designed to prevent rotation of the handle about the stylet axis when the handle and the handle-receiving means are mated together.

2. Field of the Invention

This invention relates to instruments for withdrawing samples of bone, bone marrow and other bone marrow cavity fluids from bones as in biopsy and transplant procedures.

SUMMARY OF THE INVENTION

The present invention provides a bone biopsy needle for obtaining bone samples and for withdrawing material from the bone marrow cavity which has certain very specific advantages in design and in operation. The biopsy needle of this invention consists of an elongated tubular cannula having an axially extending lumen therethrough and an elongated stylet slideably received coaxially within the cannula lumen.

The cannula has a handle positioned on its proximal end and extending perpendicularly to the axis of the cannula. The cannula handle is comprised of two equal rectangular halves extending in diametrically opposed directions to each other from the cannula axis. Each of the halves of the cannula handle has proximally extending shoulder projections substantially parallel to the axis, with one of the shoulder projections reaching closer to the cannula axis than the other should projection, so that a slot is provided on one of the halves of the cannula handle, between the cannula axis and the shoulder projection. There is an orifice in the cannula handle in flow communication and coaxial with the cannula lumen. Each of the halves of the cannula handle has a concave indentation adjacent to the elongated tubular cannula on the distally facing side of the handle to provide finger hold notches to assure a firm and secure grip by the surgeon during use. The cannula has a sharpened beveled distal end edge.

The elongated stylet has a handle positioned on its proximal end and extending perpendicularly to the axis of the cannula. The stylet handle is removably positioned on the proximal end of the cannula handle. The stylet handle includes an elongated palm contacting surface on the proximal side thereof, comprised of two equal rectangular halves extending in diametrically opposed directions to each other from the cannula axis along the same diameter and substantially to the same extent as the halves of the cannula handle. The stylet has a sharpened distal tip extending distally from the sharpened distal end edge of the cannula. The distal side of each half of the stylet handle includes a recess mated exclusively to one of the shouldered projections on the cannula handle. On one of the halves of the distal side of the stylet handle adjacent to the stylet axis, there is a tang which mates with the slot on the cannula handle to serve as an orientation device when the stylet and the cannula are matingly assembled, allowing the stylet to be inserted into the cannula lumen in one direction only and to assure proper alignment between the stylet tip and the cannula end edge. The mated stylet and cannula handles also function to allow relative movement between the two handles only in the axial direction of the cannula. When the cannula handle shoulder projections are received in the corresponding recesses of the stylet handle and the stylet tang is received in the cannula slot, rotating force may be applied around either axial direction of the stylet positioned in the cannula lumen without relative rotation between the stylet and the cannula.

A unique retention feature incorporated into the biopsy needle assembly prevents the stylet handle from becoming disassociated from the cannula handle during normal usage, yet allows the stylet handle to be easily withdrawn away from the cannula handle when required during the biopsy procedure. This is achieved by providing detent ribs 16.4 on the stylet handle which interfere slightly with the cannula handle when the two handles are matingly received together. The spring constant of the plastic used in forming the handles allows the detent ribs to releasably conform to the shape of the cannula handle and provide a slight retention force during the penetration procedure.

The proximal portion of the cannula retained within the cannula handle is provided with longitudinal flute knurling around its external perimeter. This allows the cannula to be securely held within the cannula handle when fabricated by injection molding and prevents any possible relative rotation between the cannula and the cannula handle during use.

The proximal portion of the elongated stylet retained within the stylet handle is provided with a right angle anchor bend. This allows the elongated stylet to be securely held within the stylet handle when fabricated by injection molding and prevents any possible relative rotation between the elongated stylet and the stylet handle during use.

The cannula handle and the stylet handle as described herein are designed to be able to be fabricated with bone needles (that is, mated cannula and stylet) of differing design and size, so as to be suitable for use with patients of different size and for use in different areas of the body. Thus, the cannula handle and the stylet handle as described herein may be fabricated by injection molding, for example, with a Jamshidi, or "J" needle or with an Illinois, or "I" needle. The design and function of the "J" needle and the "I" needle are well known in the art. Generally, the "J" needle is relatively longer (approximately 4 in.) and is suitable for use with adult patients and is capable of being used for obtaining both bone samples and bone marrow cavity fluids. Generally, the "I" needle is relatively shorter (approximately 1.5 in.), and is suitable for use with younger or smaller patients and is capable of being used only for obtaining bone marrow cavity fluids.

The cannula is provided with an externally ribbed neck nipple on the external perimeter of the elongated tubular cannula at the distal terminus of the cannula handle. When the bone biopsy assembly of this invention is fabricated with the relatively shorter "I" needle, the ribbed neck nipple accommodates a stop attachment. The stop attachment, preferably attached by a screw fitting, allows the biopsy needle of this invention to be used, for example in bone marrow biopsy procedures with children, where the sternum is to be penetrated, providing an effective stop to limit the depth of penetration of the biopsy needle. When the bone biopsy assembly of this invention is fabricated with the relatively longer "J" needle, the cannula neck nipple accommodates a plastic tubular tip shroud, which preferably slips on with a friction fit, to protect the cannula and stylet assembly when not in use.

A recess may also be provided on the proximal side of the cannula handle coaxial with the orifice and defined by the shoulder projections to accommodate a molded-in Luer lock. The Luer lock extends proximally from the cannula handle in the recess no farther than the proximal extent of the shoulders from the cannula handle, with the Luer lock in flow communication with the orifice. This provides a means for a clear passageway for a syringe or the like to attach to the proximal end of the cannula upon removal of the stylet.

The distal ends of the stylet, the cannula, or both are provided with sharpened cutting edge configurations enabling the needle to more readily penetrate the bone. The cutting edge configurations used on the "J" needle may be as described in U.S. Pat. No. 4,403,617, patented Sept. 13, 1983, wherein the sharpened distal end of the stylet is characterized by including an oblique concave face forming a rounded trough extending at an acute angle to, and intersecting, the axis of the stylet, and wherein the cannula terminates distally in a plurality of distally extending, axially coextensive, rounded lobes having distally sharpened edges forming a continuously curved, sinuous cutting edge. The cutting edge configurations on the "I" needle may be formed by a flat sharp cut diagonal to the axis of the mated cannula needle and elongated stylet assembly.

DETAILED DESCRIPTION OF THE PREFERRED EMBODIMENT

Figures 1, 2, 5, 6:
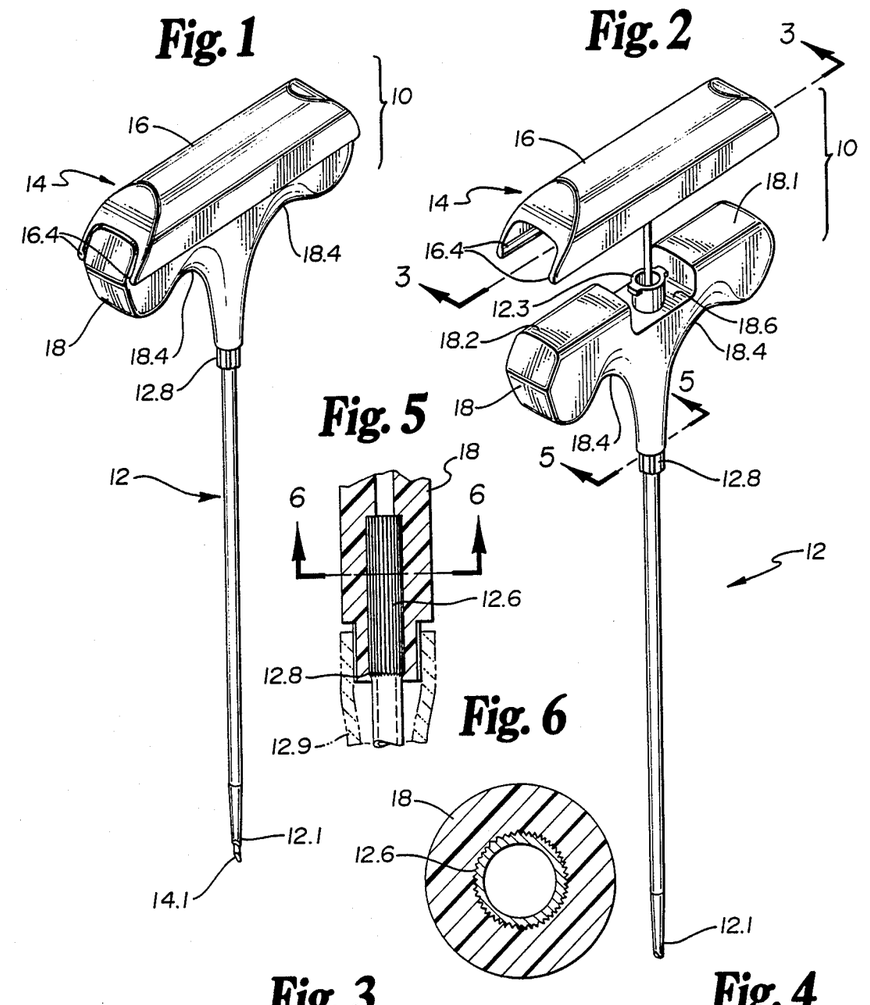
FIG. 1 is a perspective view of a bone biopsy assembly of this invention.
FIG. 2 is a perspective view of the assembly of FIG. 1 with the stylet subassembly proximally withdrawn slightly from the cannula subassembly.
FIG. 5 is a section, greatly enlarged, taken along line 5—5 of FIG. 2 detailing the neck of the cannula surrounding the flute knurled tubular cannula needle.
FIG. 6 is a sectional bottom plan view, greatly enlarged, of the neck of the cannula, showing the flute knurled perimeter of the cannula needle.

The bone biopsy assembly 10 of this invention as shown in FIGS. 1 and 2 comprises a cannula 12 having a sharpened distal end edge 12.1 within the lumen of which is slideably received a stylet 14 having a sharpened distal tip 14.1. In FIGS. 1 and 2, the reference character 12 indicates the entire separate cannula device and reference character 14 indicates the entire separate sylet device. At its proximal end, the stylet 14 is provided with a broad, palm fitting handle 16. At least the outer surface of the cannula 12 is tapered inwardly near its distal end 12.1, as shown in FIGS. 1 and 2. The inner surface (not illustrated) of the cannula 12 is also preferably tapered inwardly near its distal end 12.1. When the cannula of the bone biopsy assembly of FIG. 1 is used by itself for obtaining a bone sample, the inward taper of the distal end of the cannula serves to retain the bone sample in place as the cannula is withdrawn from the bone. The distal end 12.1 of the cannula 12 desirably fits snugly but slideably about the distal end portion 14.1 of the stylet 14 to provide a smooth external profile to facilitate the penetration of the bone biopsy needle 10 into the bone. At its proximal end, the cannula 12 is provided with a Luer lock 12.3 which is molded as an integral part of the cannula handle 18. The proximal end of the cannula 12 is also provided with a cannula handle 18 extending perpendicularly to the axis of the cannula 12 and comprised of two rectangular halves extending in diametrically opposed directions to each other from the cannula axis. Each of the halves of the cannula handle 18 has a proximally extending shouldered projection substantially parallel to the axis, with the shouldered projection 18.2 reaching closer to the axis of the cannula 12 than the shouldered projection 18.1. The shouldered projections 18.1 and 18.2 are designed to be releasably received by the mating recesses 16.1 and 16.2 on the stylet handle 16 when the stylet 14 has been inserted into the lumen of the cannula 12. A slot 18.6 is formed on the cannula handle between the shouldered projection 18.1 and the axis of the cannula. On the stylet handle, a distally projecting tang 16.6 is provided between the recess 16.1 and the axis of the stylet. The unidirectional mating between the stylet handle 16 and the cannula handle 18 and between the cannula slot 18.6 and the stylet tang 16.6 assures proper bevel alignment between the sharpened distal end edge 12.1 of the cannula 12 and the sharpened distal tip 14.1 of the stylet 14 and prevents undesirable relative rotation between the stylet 14 and the cannula 12 in use. Each of the halves of the cannula handle 18 has a concave indentation 18.4 adjacent to the elongated tubular cannula on the distally facing side of the handle to provide finger hold notches. The finger hold notches also serve to reduce the bulk of the handle. providing a light weight handle with excellent comfort and feel during use.

The stylet handle 16 extends perpendicularly to the axis of the cannula 12 and includes an elongated palm contacting surface on the proximal side thereof. The stylet handle 16 is comprised of two rectangular halves extending in diametrically opposed directions to each other from the cannula axis along the same diameter and substantially to the same extent as the halves of the cannula handle 18. At its proximal end, the stylet shaft 14, which commonly is of stainless steel, is provided with a right angle anchor bend 14.2 on the proximal terminus of the stylet shaft. This right angle anchor bend 14.2 is sufficient to securely anchor the stylet 14 in the handle which is fabricated by injection molding and also to prevent relative rotation between the stylet 14 and the stylet handle 16 during use. The stylet handle 16 and the cannula handle 18 are preferable formed from an ABS thermoplastic molding material (e.g., "Cycolac T" by Borg Warner Chemicals, Inc.).

At its proximal terminus within the cannula handle 18, the elongated tubular cannula shaft is provided with longitudinal flute knurling 12.6 around its exterior perimeter to enable it to be fixedly held within the cannula handle 18 when it is fabricated by injection molding. The exterior perimeter of the knurling 12.6 is slightly enlarged from the exterior perimeter of the body of the cannula and this assures that the cannula shaft 12 is securely held by the cannula handle 18, preventing relative rotation between the cannula shaft 12 and the cannula-handle 18 during use.

Figures 3, 4:
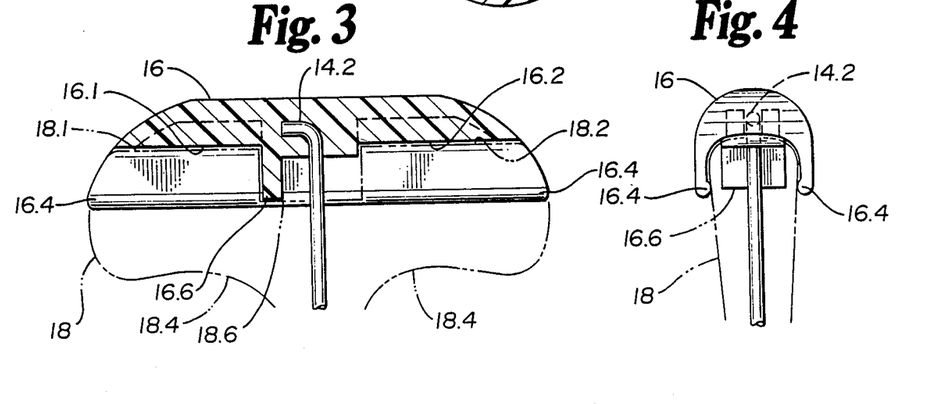
FIG. 3 is a section taken along line 3—3 of FIG. 2 and showing the cannula handle in a phantom dashed line.
FIG. 4 is a left side elevational view directly orthologic to FIG. 3.

Smoothly rounded shouldered projections 18.1 and 18.2 arise proximally from the proximal face of the cannula handle 18. The shouldered projection 18.1 reaches closer to the axis of the cannula axis than does the shouldered projection 18.2. Each of these shouldered projections 18.1 and 18.2 are shaped so as to be matingly received by a matching recess 16.1 and 16.2 respectively on the distally facing side of each half of the stylet handle. The stylet handle 16 and the cannula handle 18 can thus only be matingly received in assembly together with recess 16.1 receiving shouldered projection 18.1 and recess 16.2 receiving shouldered projection 18.2. Further, the stylet handle 16 and the cannula handle 18 can only be matingly received in assembly together with the slot 18.6 on the cannula handle receiving the tang 16.6 on the stylet handle.

A unique retention feature incorporated into the biopsy needle assembly prevents the stylet handle 16 from becoming disassociated from the cannula handle 18 during normal usage, yet allows the stylet handle 16 to be easily withdrawn away from the cannula handle 18 when required during the biopsy procedure. This is achieved by providing detent ribs 16.4 on the stylet handle 16 which interfere slightly with the cannula handle 18 when the two handles are matingly received together. The spring constant of the plastic used in forming the handles allows the detent ribs 16.4 to releasably conform to the shape of the cannula handle 18 and provide a slight retention force during the penetration procedure.

As shown in FIG. 2, the shouldered projections 18.1 and 18.2 shelter between them a Luer lock 12.3, which is molded into the cannula handle, so that even when the stylet handle 16 has been withdrawn proximally from the cannula handle 18, the syringe fitting 12.3. is prevented from contacting the planer surface upon which the cannula 12 may be placed, thereby avoiding damage to and restraining contamination of the Luer lock 12.3. Moreover, when the stylet handle 16 has been received by the cannula handle 18, the matingly received handles cooperatively protect and enclose the Luer lock 12.3. The detent ribs 16.4 completely overlap the shouldered projections 18.1 and 18.2 of the cannula handle 18 to enclose the Luer lock 12.3 protecting it from contamination during the bone penetration procedure.

When the stylet handle 16 has been matingly received by the cannula handle 18, as shown in FIG. 1, the relative lengths of the stylet 14 and the cannula 12 are such that the sharpened distal end 14.1 of the stylet 14 protrudes for a short distance beyond the sharpened distal end edge 12.1 of the cannula 12.

Figures 7, 8, 9, 10, 11:
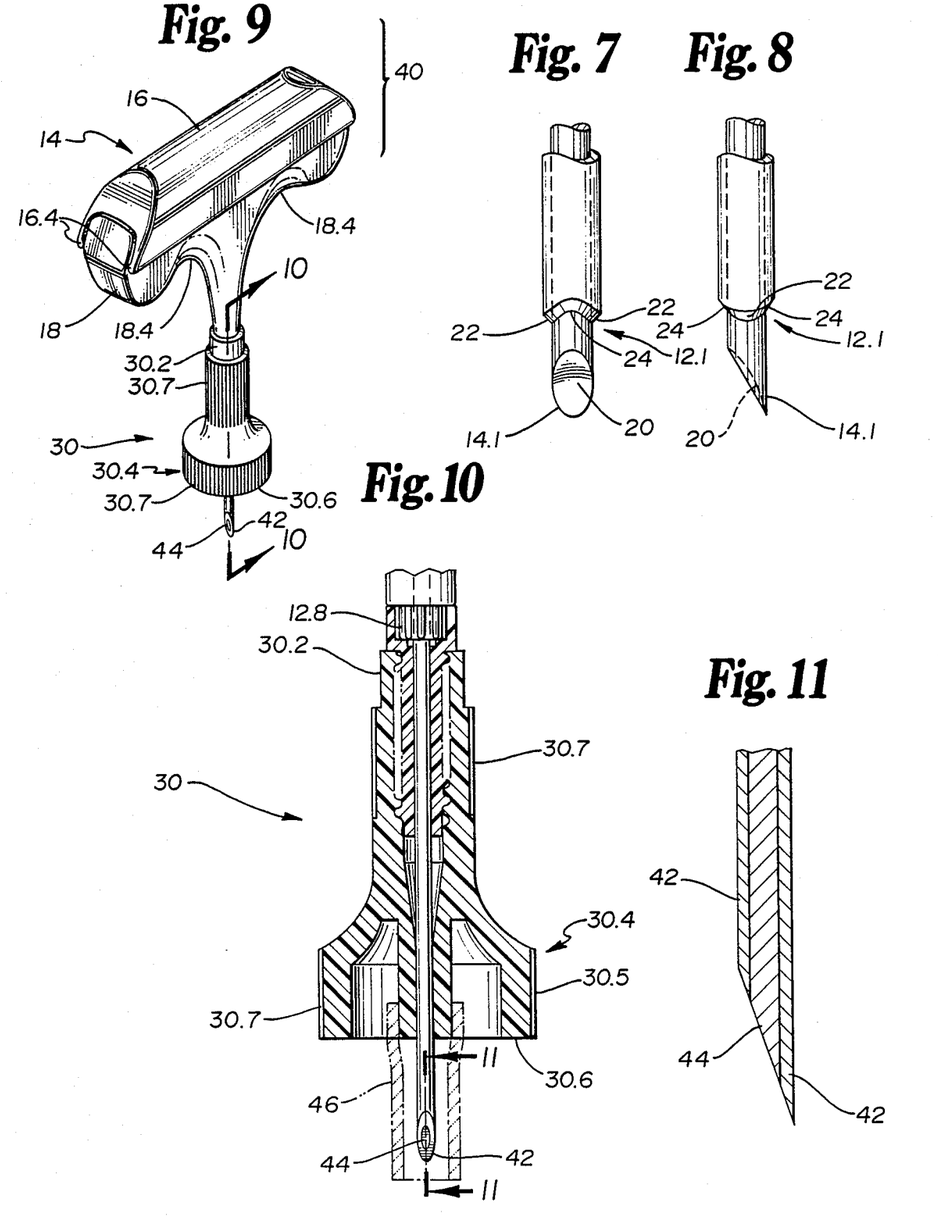
FIG. 7 is a front elevational view of the tip of the stylet-cannula assembly of FIG. 1, greatly enlarged.
FIG. 8 is a left side elevational view orthologic to the view of FIG. 7.
FIG. 9 is a perspective view of an alternative form of the bone biopsy assembly of this invention.
FIG. 10 is a vertical cross section taken along line 10—10 of FIG. 9.
FIG. 11 is a sectional view taken along line 9—9 of FIG. 10.

As shown in FIGS. 1, 6 and 9, the stylet is desirably circular in cross-section. The solid distal end of the stylet is beveled at an acute angle to the axis of the stylet to form an oblique face 20 extending across the width of the stylet shaft. The oblique face is concave, i.e., it forms a trough extending between the point and the tip of the stylet, the trough extending at an acute angle to and intersecting the axis of the stylet, as illustrated in FIGS. 7 and 8 and as described in U.S. Pat. No. 4,403,617, patented Sept. 13, 1983, which is incorporated herein by reference.

The cannula 12 is preferably in the form of an elongated hollow tube having an axially extending lumen therethrough, of circular cross-section throughout the majority of its length. The walls adjacent the distal end of the cannula taper inwardly slightly a short distance from the sharpened end of the cannula. The inner surface of the cannula 12 is also preferably tapered inwardly near its distal end. When the cannula as shown in FIG. 1 is used by itself for obtaining a bone sample, the inward taper of the distal end of the cannula serves to retain the bone sample within the cannula lumen as the cannula is retracted.

The distal end of the cannula, as shown in FIGS. 1, 7 and 8, is provided with distally extending, distally coextensive convex chamfered lobes 22. The convex chamfered lobes are gently rounded, separated by concave chamfered areas 24 with the edges merging into one another as shown in FIGS. 7 and 8. If the cannula were to be axially split and unrolled, the distal edge of cannula formed by the convex chamfered lobes and the concave chamfered areas between the lobes would form a generally sinusoidal curve. The distal end of the cannula may appropriately be ground to render the continuous sinuous distal edge of the cannula extremely sharp. This particular sinuously curve edged cannula is further described in U.S. Pat. No. 4,403,617, patented Sept. 13, 1983.

The distal end of the cannula as shown in FIGS. 9 to 11 is provided with a bone penetrating cutting edge formed by a flat sharp cut diagonal to the axis of the mated cannula needle 42 and elongated stylet 44 assembly.

The distal tip 14.1 of the stylet, when inserted into the lumen of the cannula protrudes from the distal end edge 12.1 of the cannula 12, the opening at the distal end of the cannula fitting snugly but slideably about the periphery of the stylet so that the outer surfaces of the stylet and cannula merge into one effective bone penetrating and cutting tool.

To facilitate its use with patients of different size and in different areas of the body, the bone biopsy assembly of this invention may be fabricated according to the alternative embodiment invention as illustrated in FIGS. 9 to 11. According to the embodiment as shown in FIGS. 9 and 10, the bone biopsy assembly is provided with a stop attachment to regulate the depth of penetration to be achieved. The cannula is thus provided with an externally preferably longitudinally ribbed neck nipple 12.8 on the external perimeter of the elongated tubular cannula at the distal terminus of the cannula handle 18 to releasably receive a stop attachment 30. The stop attachment 30 comprises an elongated tubular externally threaded extension 30.2 which is glued or otherwise fixedly attached to the neck nipple 12.8. The internal diameter of the stop attachment 30 is sized to closely accommodate the external diameter of the cannula 12. The internal diameter of the proximal terminus of the threaded extension 30.2 is sized to fit with the neck nipple 12.8. The external threading of the extension 30.2 engages the internal threading of a penetration stop guide 30.4 which preferably terminates distally in a flared skirt 30.5 with a rim stop 30.6 to limit the depth of penetration of the bone biopsy assembly when used for example with children where the sternum is to be penetrated. The stop guide 30.4 may be screwed up or down on the threaded extension 30.2 to expose the desired length of the needle assembly. To facilitate a non-slip grip during its engagement and disengagement, the exterior of the stop guide 30.4 is provided with flute knurling 30.7. The stop attachment can accommodate a plastic tubular tip shroud 46, which preferably fits on with a friction fit, to protect the cannula and stylet assembly when not in use.

In using the bone biopsy needle of this invention, the bone biopsy assembly 10 as shown in FIG. 1 or the assembly 40 as shown in FIG. 9 is grasped firmly by the cannula handle 18, with the broad palm-contacting surface of the stylet handle 16 firmly received in the palm of the physician and fingers wrapped about the finger gripping surface of the cannula handle 18, utilizing the finger hold notches 18.4 on either side of the axis of the cannula to further assure a firm, non-slip grip during the surgical procedure. The index finger may desirably be aligned along the length of the cannula to assure greater accuracy and control during the bone penetration. The thumb may also be wrapped around the assembled stylet and cannula handles to assure greater control and leverage. The distal end of the sharpened stylet and cannula assembly enters through the skin and intervening tissue to encounter the outer surface of the bone. Significant distal and rotative forces are then exerted on the stylet and cannula handle assembly in a controlled manner to cause the sharpened distal ends of a the stylet and cannula assembly to penetrate through the hard outer bone material and enter the bone marrow containing cavity. When it is desired to obtain a bone sample, the cannula 12 as illustrated in FIG. 1 is used alone. Penetration of the hard outer bone material is accomplished in the manner just described, at which point the cannula, holding the bone sample in the lumen thereof, is smoothly withdrawn and the bone sample is dislodged, as with a wire obturator, for further analysis.

During the bone marrow cavity penetration procedure, it is the stylet handle 16 which receives most of the rotative and penetrating forces applied by the surgeon's hand, with the cannula 12 responding operatively to the pressures transmitted to the cannula handle 18. Also, the perpendicularly extending portions of the assembled stylet and cannula handles function as levers during the penetrating procedure, allowing the surgeon to exert the necessary rotative and axial force to achieve penetration to the interior bone cavity. When the bone biopsy assembly as shown in FIG. 9 is used, as with children where the sternum is to be penetrated, the rim of the stop guide will limit the depth of penetration of the bone biopsy needle once the rim contacts the skin of the patient.

Once the bone marrow cavity has been entered by the sharpened end of the bone biopsy needle assembly, the stylet 14 is gently removed proximally from the cannula lumen while holding the cannula 12 firmly positioned in the bone. The detent ribs 16.4 of the stylet handle 16 which, during the bone penetration procedure, assure that the cannula handle 18 and the stylet handle 16 assembly function securely together, now allow the stylet 14 to be easily and smoothly retracted from the cannula lumen without disturbing the position of the cannula 12 in the bone. After the retraction of the stylet 14, the Luer lock 12.3 axially situated between the shouldered projections 18.1 and 18.2 of the cannula handle 18 is exposed and a standard hypodermic syringe, not illustrated, can be attached thereto in the conventional manner. Retraction of the plunger of the hypodermic syringe causes a sample of bone marrow to be drawn into the syringe lumen for diagnostic examination or use in transplant procedures. The cannula and the hypodermic syringe containing the bone marrow sample can then be withdrawn simultaneously and the marrow contents discharged in an appropriate manner.

As has been described, the detent ribs 16.4 of the stylet handle 16 substantially overlap the cannula handle 18 allowing essentially all of the force of pressure during the penetration procedure to be transmitted through the cannula handle 18 to the sharpened distal end of the bone biopsy assembly. Additionally, the detent ribs 16.4 of the stylet handle 16 and the cannula handle 18 in assembly function together to protectively enclose the Luer lock 12.3 reducing the possibility of contamination thereto during the procedure. Further the shouldered projections 18.1 and 18.2 of the cannula handle 18 are received by the individually mated recesses 16.1 and 16.2 of the stylet handle 16 and the stylet handle tang 16.6 is received by the cannula handle slot 18.5 in one direction only to assure proper bevel alignment between the sharpened distal tip of the stylet 44 and the sharpened distal end edge of the cannula 42. This unique cooperative fit between the stylet handle 16 and the cannula handle 18 also functions to prevent relative rotation between the stylet 14 and the cannula 12 during the rotational twisting forces exerted in penetrating the bone. The bone biopsy needle of this invention is suitable for use in either hand and can be rotated in either direction around its axis without the possibility of the stylet handle 16 and cannula handle 18 becoming dislodged from each other. The Luer lock 12.3 disposed between the shouldered projections of the cannula handle is recessed below the proximal extent of the shouldered projections 18.1 and 18.2 so that there is no transmission of force onto the Luer lock, thus avoiding any possible damage thereto. The stop attachment 30 in the alternative embodiment of FIGS. 9 to 11 functions to limit the depth of penetration of the bone biopsy needle, thus making it suitable for use with patients of different size and in different areas of the body. The close tapered fit between the sharpened distal end edge of the cannula about the sharpened distal tip of the stylet allow the axial pressure imparted by the sharpened distal end of the bone biopsy needle assembly to be concentrated from the axial force imparted over the entire surface of the handle of the assembly.

The insert molding of the longated tubular cannula into the cannula handle with longitudinal flute knurling around the external perimeter of the proximal portion of the cannula retained within the handle provides exceptional torque and pull-out resistance. Similarly, the insert molding of the elongated stylet into the stylet handle with the right angle anchor bend on the proximal portion of the stylet retained within the stylet handle also provides exceptional torque and pull-out resistance. The resistance of the cannula to torque and pull-out stress has been demonstrated in test procedures. 120 cannulas according to this invention were prepared by insert molding cannulas of varying standard sizes into the handle as described herein. The cannulas were inserted approximately 1 inch into the plastic handles, using ABS for the handles. Approximately 24 hours after molding, the samples were tested for torque resistance with a standard torque-tester using standard operating procedures and a calibrated torque meter. Samples of each size were also tested for pull-out strength using an Instron Tensile Testor$v$ at a crosshead speed of 10 ipm. All of the samples exhibited excellent torque-resistance and pull-out strength with extremely high reliability and consistency.

What is claimed is:

1. A bone biopsy needle assembly, comprising:
   (a) an elongated tubular cannula having an axially extending lumen therethrough and having distal and proximal ends;
   (b) a cannula handle having proximal and distal sides positioned on the proximal end of said cannula, a proximal portion of the proximal end of the cannula retained within the cannula handle, said proximal portion of the cannula being provided with longitudinal flute knurling around the external perimeter of said cannula for allowing the cannula to be securely held within the cannula handle by injection insert molding; wherein
   (c) said cannula handle extends perpendicularly to the axis of said cannula; and wherein
   (d) said cannula handle is comprised of two equal generally rectangular halves extending in diametrically opposed directions to each other from said cannula axis;
   (e) each of said equal halves of said cannula handle having proximally extending shoulder projections substantially parallel to the axis with one of the said shoulder projections reaching closer to the cannula axis than the other said shoulder projection, with a distally extending slot formed between one of the shoulder projections and the cannula axis;
   (f) an orifice in said cannula handle in flow communication with said cannula lumen, said orifice being coaxial with said cannula lumen;
   (g) a stylet handle having distal and proximal sides removably positioned on the proximal end of said cannula handle, wherein
   (h) said stylet handle extends perpendicularly to the axis of said cannula and includes an elongated palm contacting surface on the proximal side thereof; and wherein
   (i) said stylet handle is comprised of two equal generally rectangular halves extending in diametrically opposed directions to each other from said cannula axis along the same diameter and substantially to the same extent as said equal halves of said cannula handle;
   (j) an elongated stylet extending from the distal side of said stylet handle and slidably received within said cannula lumen, said stylet being retained within said stylet handle by injection insert molding and terminating in an anchor bend at a distal terminus within said stylet handle, and said stylet having a sharpened distal tip which extends distally from the distal end of said cannula and said cannula having a sharpened beveled distal end edge;
   (k) and wherein the distal side of each of said equal halves of said stylet handle further includes a recess means, each of said recess means being mated exclusively to one of said shoulder projections with a distally extending tang formed between one of the recesses and the stylet axis, said tang being matingly received by the slot on the cannula handle when the shoulder projections are mated with the recess means, thus allowing relative movement between the stylet and cannula handles only in the axial direction of said cannula and assuring bevel alignment between the sharpened beveled distal end edge of the cannula and the sharpened distal tip of the stylet;
   (l) whereby when said shouldered projections on said cannula handle halves are received in the exclusively mated recesses of said stylet handle halves, force may be rotatingly applied around either axial direction of said elongated stylet positioned in said elongated cannula lumen without relative rotation between said elongated stylet and said elongated cannula.

2. The bone biopsy needle assembly of claim 1, further comprising:
   (a) a recess on the proximal side of said cannula handle and defined by said shouldered projections of said cannula handle which is coaxial with said orifice;
   (b) a syringe fitting molded into the cannula handle proximally extending from said cannula handle in said recess to an extent no more than the proximal extent of the shouldered projections for said cannula handle; and wherein
   (c) said syringe fitting is in flow communication with said orifice; and
   (d) said stylet handle further includes detent ribs on the distal side releasably conforming to the external shape of the cannula handle for covering a proximal end of the syringe fitting when said recess means and shoulder projections are mated.

3. The bone biopsy needle assembly of claim 1, further comprising:
   (a) a concave indentation on each half of the cannula handle adjacent to the elongated tubular cannula on the distal side of the cannula handle for finger hold notches;
   (b) said sharpened distal end of the stylet includes an oblique, concave face forming a trough extending at an acute angle to and intersecting the axis of the stylet; and (c) said sharpened beveled end edge of the cannula terminates in a plurality of distally extending, axially coextensive, rounded lobes having distally sharpened edges.

4. The bone biopsy needle assembly of claim 1, wherein the cannula handle and the stylet handle are formed of ABS thermoplastic material and the cannula and the stylet are formed of stainless steel, and wherein the cannula is retained within the cannula handle and the stylet is retained within the stylet handle by injection insert molding.

5. The bone biopsy needle assembly of claim 1, further comprising:
(a) an externally ribbed neck nipple on the external perimeter of the cannula at a distal terminus of the cannula handle; and
(b) a stop attachment having distal and proximal termini received by said neck nipple, the distal terminus of the stop attachment being less than the distal terminus of the cannula; wherein
(c) said stop attachment is comprised of an elongated tubular externally threaded extension and an internally threaded penetration stop guide; wherein
(d) the internal diameter of a major distal portion of the threaded extension is sized to the external diameter of the cannula and the internal diameter of a proximal terminus of the threaded extension is sized to fit with the neck nipple and is fixedly attached thereto;
(e) the external threading of the threaded extension releasably engages the internal threading of the penetration stop guide, said penetration stop guide terminating distally in a penetration stop means to limit the depth of penetration of the bone biopsy needle; and
(f) said penetration stop guide adapted releasably receive a tubular shroud for protecting the bone biopsy needle when not in use.

6. A bone biopsy needle assembly of claim 5, wherein
(a) the sharpened distal end of the cannula and stylet in assembly is formed by a flat sharp acute angle cut diagonal to the axis of the mated cannula and stylet assembly; and
(b) the correct bevel alignment between the sharpened beveled distal end edge of the cannula and the sharpened distal tip of the stylet is assured by the mating received slot on the cannula handle with the tang on the stylet handle.

7. A bone biopsy needle assembly of claim 1, further comprising an externally ribbed neck nipple on the exterior perimeter of the cannula at the distal terminus of the cannula handle, said neck nipple designed to releasably receive a tubular shroud for protecting the bone biopsy needle when not in use.

8. A bone biopsy needle assembly comprising:
(a) an elongated tubular cannula having an axially extending lumen therethrough;
(b) a cannula handle positioned on the proximal end of said cannula, the proximal portion of the cannula retained within the cannula handle being provided with longitudinal flute knurling around the external perimeter of the said cannula, allowing the cannula to be securely held within the cannula handle to be securely held within the cannula handle by injection molding; wherein
(c) said cannula handle extends perpendicularly to the axis of said cannula; and wherein
(d) said cannula handle is comprised of two equal rectangular halves extending in diametrically opposed directions to each other from said cannula axis;
(e) an orifice in said cannula handle in flow communication with said cannula lumen, said orifice being coaxial with said cannula lumen;
(f) a stylet handle removably positioned on the proximal end of said cannula handle; wherein
(g) said stylet handle extends perpendicularly to the axis of said cannula and includes an elongated palm contacting surface on the proximal side thereof; and wherein
(h) said stylet handle is comprised of two equal rectangular halves extending in diametrically opposed directions to each other from said cannula axis along the same diameter and substantially to the same extend as said equal halves of said cannula handle;
(i) an elongated stylet extending from the distal side of said stylet handle and slidably received within said cannula lumen, said stylet being retained within said stylet handle by injection molding and terminating in an anchor bend at its distal terminus within said stylet handle, and said stylet having a sharpened distal tip which extends distally from the distal end of said cannula and said cannula having a sharpened beveled distal end edge;
(j) wherein the distal side of each of said equal halves of said stylet handle further includes means for being mated exclusively to the proximal side of only one of said equal halves of said cannula handle, thus assuring bevel alignment between the sharpened beveled distal end edge of the cannula and the sharpened distal tip of the stylet;
(k) a recess on the proximal side of said cannula handle which is coaxial with said orifice;
(l) a syringe fitting in flow communication with said orifice molded into the cannula handle proximally extending from said cannula handle in said recess to an extent no more than the proximal extent of the cannula handle;
(m) an externally ribbed neck nipple of the external perimeter of the cannula at the distal terminus of the cannula handle; and
(n) a stop attachment comprised of an elongated tubular externally threaded extension and an internally threaded penetration stop guide received by said neck nipple, the distal terminus of the stop attachment being less than the distal terminus of the cannula; wherein
(o) the internal diameter of a major distal portion of the threaded extension is sized to the external diameter of the cannula and the internal diameter of a proximal terminus of the threaded extension is sized to fit with the neck nipple and is fixedly attached thereto;
(p) the external threading of the threaded extension releasably engages the internal threading of the penetration stop guide, said penetration stop guide terminating distally in a penetration stop means to limit the depth of penetration of the bone biopsy needle; and
(q) said penetration stop guide adapted to releasably receive a tubular shroud for protecting the bone marrow biopsy needle when not in use.

9. A bone biopsy needle assembly of claim 8, wherein
(a) the sharpened distal end of the cannula and stylet in assembly is formed by a flat sharp acute angle cut diagonal to the axis of the mated cannula and stylet assembly and
(b) the correct bevel alignment between the sharpened beveled distal end edge of the cannula and the sharpened distal tip of the stylet is assured by the mating alignment of the cannula handle with the stylet handle.

10. A bone biopsy needle assembly of claim 8, further comprising an externally ribbed neck nipple on the exterior perimeter of the cannula at the distal terminus of the cannula handle, said neck nipple designed to releasably receive a tubular plastic shroud for protecting the bone marrow biopsy needle when not in use.

* * * * *

UNITED STATES PATENT AND TRADEMARK OFFICE
CERTIFICATE OF CORRECTION

PATENT NO. : 4,838,282

DATED : June 13, 1989

INVENTOR(S) : Robert K. Strasser and Robert L. Netsch

It is certified that error appears in the above-identified patent and that said Letters Patent is hereby corrected as shown below:

Column 9, line 46, claim 1, after "of" insert --the--

Column 10, line 52, claim 2, delete "for" and insert --from--

Column 11, line 38, claim 5, after "adapted" insert --to--

Column 11, line 67, claim 8, after "handle" delete "to be securely held within the cannula handle"

Column 12, line 20, claim 8, after "same" delete "extend" and insert --extent--.

Signed and Sealed this

Third Day of April, 1990

Attest:

HARRY F. MANBECK, JR.

Attesting Officer

Commissioner of Patents and Trademarks